United States Patent
Savall et al.

(10) Patent No.: US 12,089,911 B2
(45) Date of Patent: *Sep. 17, 2024

(54) USER INTERFACE DEVICE HAVING FINGER CLUTCH

(71) Applicant: Verb Surgical Inc., Santa Clara, CA (US)

(72) Inventors: Joan Savall, Palo Alto, CA (US); Allegra Anna Lenta Shum, San Francisco, CA (US)

(73) Assignee: Verb Surgical Inc., Santa Clara, CA (US)

( * ) Notice: Subject to any disclaimer, the term of this patent is extended or adjusted under 35 U.S.C. 154(b) by 412 days.

This patent is subject to a terminal disclaimer.

(21) Appl. No.: 17/492,506

(22) Filed: Oct. 1, 2021

(65) Prior Publication Data

US 2022/0022988 A1 Jan. 27, 2022

Related U.S. Application Data

(63) Continuation of application No. 16/010,020, filed on Jun. 15, 2018, now Pat. No. 11,135,030.

(51) Int. Cl.
*A61B 34/30* (2016.01)
*A61B 17/29* (2006.01)
(Continued)

(52) U.S. Cl.
CPC .............. *A61B 34/74* (2016.02); *A61B 17/29* (2013.01); *A61B 34/20* (2016.02); *A61B 34/35* (2016.02);
(Continued)

(58) Field of Classification Search
CPC ......... A61B 34/20; A61B 34/30; A61B 34/35; A61B 2034/741; A61B 2034/742;
(Continued)

(56) References Cited

U.S. PATENT DOCUMENTS

| 5,305,017 A | 4/1994 | Gerpheide |
| 6,587,750 B2 | 7/2003 | Gerbi et al. |

(Continued)

FOREIGN PATENT DOCUMENTS

| CN | 1921810 A | 2/2007 |
| CN | 101610877 A | 12/2009 |

(Continued)

OTHER PUBLICATIONS

Notification of Reasons for Refusal mailed on Feb. 15, 2022 from related Japanese Patent Application No. 2020-569939, 12 pages including translation.

(Continued)

*Primary Examiner* — Masud Ahmed
(74) *Attorney, Agent, or Firm* — Aikin & Gallant, LLP

(57) ABSTRACT

User interface devices for manipulating a robotic surgical tool in a surgical robotic system are described. A user interface device can include a device housing having a gripping surface symmetrically disposed about a central axis. The gripping surface can include a surface of revolution about the central axis. A tracking sensor can be mounted within the device housing to generate spatial state signals in response to movement of the device housing. The spatial state signals can be used to control motion of robotic system actuators. A finger clutch can be disposed at an end of the device housing, and can generate a clutch signal in response to a touch by a user. The clutch signal can be used to pause the motion of the robotic system actuators. Other embodiments are also described and claimed.

20 Claims, 10 Drawing Sheets

(51) Int. Cl.
| | |
|---|---|
| *A61B 34/00* | (2016.01) |
| *A61B 34/20* | (2016.01) |
| *A61B 34/35* | (2016.01) |
| *A61B 34/37* | (2016.01) |
| *B25J 13/02* | (2006.01) |
| *B25J 13/08* | (2006.01) |
| *G06F 3/0346* | (2013.01) |
| *A61B 17/00* | (2006.01) |

(52) U.S. Cl.
CPC ............... *A61B 34/37* (2016.02); *B25J 13/02* (2013.01); *B25J 13/08* (2013.01); *G06F 3/0346* (2013.01); *A61B 2017/00039* (2013.01); *A61B 2017/00075* (2013.01); *A61B 2017/00199* (2013.01); *A61B 2017/00207* (2013.01); *A61B 2017/00212* (2013.01); *A61B 2017/00221* (2013.01); *A61B 2017/00398* (2013.01); *A61B 2017/0042* (2013.01); *A61B 2034/2048* (2016.02); *A61B 2034/2051* (2016.02); *A61B 2034/742* (2016.02); *A61B 2034/743* (2016.02)

(58) Field of Classification Search
CPC ... A61B 2034/744; A61B 34/74; A61B 17/29; A61B 34/37; A61B 2017/00039; A61B 2017/00075; A61B 2017/00199; A61B 2017/00207; A61B 2017/00212; A61B 2017/00221; A61B 2017/00398; A61B 2017/0042; A61B 2034/2048; A61B 2034/2051; A61B 2034/743; G06F 3/03547; G06F 3/0346; B25J 13/02; B25J 13/08

See application file for complete search history.

(56) References Cited

U.S. PATENT DOCUMENTS

| | | | |
|---|---|---|---|
| 6,659,939 B2 | 12/2003 | Moll et al. | |
| 6,995,744 B1 | 2/2006 | Moore et al. | |
| 7,206,627 B2 | 4/2007 | Abovitz et al. | |
| 7,865,266 B2 | 1/2011 | Moll et al. | |
| 8,332,072 B1 | 12/2012 | Schaible et al. | |
| 8,391,954 B2 | 3/2013 | Quaid, III | |
| 8,521,331 B2 | 8/2013 | Itkowitz | |
| 8,682,489 B2 | 3/2014 | Itkowitz | |
| 8,831,782 B2 | 9/2014 | Itkowitz | |
| 8,930,027 B2 | 1/2015 | Schaible et al. | |
| 9,002,517 B2 | 4/2015 | Bosscher et al. | |
| 9,108,318 B2 | 8/2015 | Diolaiti | |
| 9,241,768 B2 | 1/2016 | Sandhu et al. | |
| 10,532,466 B2* | 1/2020 | Schaible ............... | A61B 34/76 |
| 11,065,069 B2* | 7/2021 | Kang ................... | A61B 34/32 |
| 2001/0011995 A1 | 8/2001 | Hinckley et al. | |
| 2007/0013336 A1 | 1/2007 | Nowlin et al. | |
| 2008/0071293 A1 | 3/2008 | Zalenski et al. | |
| 2008/0154246 A1 | 6/2008 | Nowlin et al. | |
| 2010/0092267 A1 | 4/2010 | Najdovski et al. | |
| 2010/0228264 A1 | 9/2010 | Robinson et al. | |
| 2010/0302140 A1 | 12/2010 | Araki et al. | |
| 2011/0022229 A1 | 1/2011 | Jang et al. | |
| 2011/0118748 A1* | 5/2011 | Itkowitz ................ | A61B 90/98 606/130 |
| 2011/0118752 A1 | 5/2011 | Itkowitz | |
| 2011/0306986 A1 | 12/2011 | Lee et al. | |
| 2012/0059519 A1 | 3/2012 | Kishi | |
| 2012/0071891 A1 | 3/2012 | Itkowitz et al. | |
| 2012/0071892 A1 | 3/2012 | Itkowitz et al. | |
| 2013/0166030 A1 | 6/2013 | Biedermann et al. | |
| 2014/0018960 A1 | 1/2014 | Itkowitz | |
| 2014/0094968 A1 | 4/2014 | Taylor et al. | |
| 2014/0148820 A1 | 5/2014 | Ogawa et al. | |
| 2014/0277747 A1 | 9/2014 | Walker et al. | |
| 2015/0133940 A1 | 5/2015 | Palmer et al. | |
| 2016/0066907 A1 | 3/2016 | Cheney et al. | |
| 2016/0199060 A1 | 7/2016 | Morgan et al. | |
| 2017/0095298 A1* | 4/2017 | Vakharia ............ | A61B 18/1445 |
| 2017/0239008 A1 | 8/2017 | Namiki | |
| 2017/0312043 A1 | 11/2017 | Ogawa et al. | |
| 2018/0078319 A1 | 3/2018 | Nobles | |
| 2018/0168759 A1 | 6/2018 | Kilroy et al. | |
| 2018/0368836 A1* | 12/2018 | Auld .................. | A61B 17/1155 |
| 2019/0142416 A1 | 5/2019 | Cheney et al. | |
| 2019/0380802 A1 | 12/2019 | Savall et al. | |
| 2020/0152190 A1* | 5/2020 | Itkowitz ................ | G10L 15/22 |

FOREIGN PATENT DOCUMENTS

| | | |
|---|---|---|
| CN | 103169552 A | 6/2013 |
| CN | 106572851 A | 4/2017 |
| CN | 107708595 A | 2/2018 |
| JP | 2018509210 A | 4/2018 |
| WO | 2014/197265 A1 | 12/2014 |
| WO | 2016154173 A1 | 9/2016 |
| WO | 2018107062 A1 | 6/2018 |

OTHER PUBLICATIONS

Examiner's Decision of Refusal mailed on Oct. 4, 2022 from related Japanese Patent Application No. 2020-569939, 8 pages including translation.

Office Action received for Chinese Patent Application No. 201880094460.1, mailed on Feb. 28, 2023, 24 pages (13 pages of English Translation and 11 pages of Original Document).

Office Action received for European U.S. Appl. No. 18/742,874, mailed on May 2, 2023, 4 pages.

Office Action received for Japanese Patent Application No. 2020-569939, mailed on Feb. 24, 2023, 3 pages.

EPO Communication Pursuant to Rules 161(1) and 162 EPC from related EP Application No. 18742874.3 dated Dec. 17, 2020, 3 pages.

PCT International Search Report and Written Opinion from related PCT Application No. PCT/US2018/037943 mailed Mar. 20, 2019, 11 pages.

PCT International Preliminary Report on Patentability from related PCT Application No. PCT/US2018/037943 mailed Dec. 24, 2020, 7 pages.

Office Action received for Chinese Patent Application No. 201880094460.1, mailed on Oct. 20, 2023, 16 pages (7 pages of English Translation and 9 pages of Original Document).

Office Action received for Chinese Patent Application No. 201880094460.1, mailed on Jan. 24, 2024, 21 pages (10 pages of English Translation and 11 pages of Original Document).

Office Action received for Japanese Patent Application No. 2023-012711, mailed on Jan. 9, 2024, 6 pages (3 pages of English Translation and 3 pages of Original Document).

Intention to grant received for European Patent Application No. 18742874.3, mailed on May 14, 2024, 6 pages.

Office Action received for Chinese Patent Application No. 201880094460.1, mailed on Mar. 29, 2024, 19 pages (8 pages of English Translation and 11 pages of Original Document).

* cited by examiner

USER INTERFACE DEVICE HAVING FINGER CLUTCH

This application is a continuation of co-pending U.S. patent application Ser. No. 16/010,020, filed on Jun. 15, 2018, which application is hereby incorporated herein by reference in its entirety.

BACKGROUND

Field

Embodiments related to robotic systems, are disclosed. More particularly, embodiments related to surgical robotic systems and corresponding user interface devices, are disclosed.

Background Information

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools.

A surgical robotic system may be remotely operated by a surgeon to command a robotically-assisted tool located at an operating table. The surgeon may use a computer console located in the operating room, or it may be located in a different city, to command a robot to manipulate the surgical tool mounted on the operating table. The robotically-controlled surgical tool can be an endoscope mounted on a robotic arm. Accordingly, the surgical robotic system may be used by the remote surgeon to perform an endoscopic surgery.

The surgeon may provide input commands to the surgical robotic system, and one or more processors of the surgical robotic system can control system components in response to the input commands. For example, the surgeon may hold in her hand a user input device such as a joystick or a computer mouse that she manipulates to generate control signals to cause motion of the surgical robotic system components, e.g., an actuator, a robotic arm, and/or a surgical tool of the robotic system.

SUMMARY

A conventional user interface device for a surgical robotic system includes a grip that a surgeon manipulates using her hand, to generate an input command to move an actuator, to which a robotic surgical tool and/or end effector is coupled in the surgical robotic system. The surgeon can move the grip within a workspace, such as a range of motion of a linkage system connected to the grip, to remotely cause a corresponding movement of the actuator. When a limit of the workspace is reached, e.g., when the linkage system is fully extended, the surgeon can press a clutch button to disconnect the input from the surgical robotic system. That is, when the clutch button is pressed, the grip can be repositioned within the workspace without causing movement of the actuator. In order to actuate the clutch button, however, the surgeon must apply a force large enough to counter a return spring force of the clutch button. For example, the surgeon must press downward on the clutch button. The downward pressure may cause unintentional movement of an end effector because the grip might also be simultaneously pushed downward. Unintentional movement of the grip can produce imprecise surgical maneuvers at the end effector. Thus, a user interface device for use in robotic surgery is needed that reduces a likelihood of unintentional movements of the corresponding, remote actuator.

A user interface device for controlling a surgical robotic system is provided that does not require an actuation force and reduces a likelihood of unintentional movement of the corresponding actuator. In an embodiment, the user interface device includes a device housing having a radially-symmetric gripping surface to allow a user to comfortably hold the device housing in her hand in any orientation. For example, the gripping surface may include a surface of revolution having a surface contour revolved about a central axis. In one instance, the surface of the housing defines an ellipsoid, in which case the central axis may be the longitudinal or major axis of the ellipsoid. A tracking sensor and/or a gripping sensor may be mounted within the device housing. The tracking sensor may generate spatial state signals in response to movement of the device housing, and the gripping sensor may generate a grip signal in response to being squeezed. The spatial state signals can track movement of the device housing in six degrees of freedom. The spatial state signals and the grip signal may then be used by the system to control movement of a remote robotic arm (and a surgical tool mounted on the arm). For example, the spatial state signal can be input to the surgical robotic system for controlling motion of the robotic surgical tool. The user interface device may include a finger clutch having a capacitive sensor therein, which is used to generate a clutch signal. The clutch signal can be generated in response to detection, using the capacitive sensor, of a user touch of the finger clutch. The clutch signal is then used by the system to pause all movement of the surgical tool regardless of a change in the spatial state signals or the grip signal. The finger clutch can be configured to, when pressed, generate the clutch signal to pause motion regardless of the spatial state signals.

The finger clutch may be mounted on an end of the device housing to be easily reached by an extended finger of the user. The capacitive sensor may include a conductive pad extending around the central axis. The conductive pad is part of an electrode structure mounted at the end of the housing whose capacitance changes in response to the user touch. This change in capacitance can be detected using an electronic sensor circuit (e.g., contained within the housing), that generates the clutch signal based on having detected the capacitance change, e.g., a bi-stable signal having two states, namely "clutch activation" when a capacitance change has been detected, or "clutch deactivation" when the capacitance change has not been detected.

In an embodiment, the finger clutch is also radially-symmetric about the central axis. The finger clutch can be shaped to allow the user to easily touch a capacitive sensing region (having the conductive pad that is formed on the finger clutch). For example, the finger clutch may have a frustoconical shape. The capacitive sensor of the finger clutch can include one or more conductive pads covered by an electrically insulating clutch cover around the frustoconical shape. Accordingly, when the user's finger touches the clutch cover over the conductive pad, the capacitance of the conductive pad changes.

In an embodiment, the user interface device includes an electronic processor to generate the clutch signal. The user interface device processor can be configured to detect the change of capacitance, for example, through processing of a digitized version of a capacitive sensor signal that may be produced by a capacitive sensing amplifier circuit (which may be deemed to be part of the UID processor). When a capacitance change is above a predetermined threshold capacitance, or when a capacitance change lasts a predetermined period of time, the user interface device processor may determine that the user has touched the clutch cover and so asserts the clutch signal. This is also referred to as determining whether or not a predetermined touch gesture has occurred. The clutch signal is then used by the system to pause all motion of the remote robotic arm (and the surgical tool mounted on the arm).

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Embodiments describe a user interface device (UID) usable by a robotic system to control actuators that move a robotic arm or a tool. The robotic system can be a surgical robotic system, the robotic arm can be a surgical robotic arm, and the tool can be a surgical tool. The UID may, however, be used by other systems, such as interventional cardiology systems, vision systems, or aircraft systems, to control other output components. These other systems name only a few possible applications.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of a UID to a specific configuration described in the various embodiments below.

In an aspect, a UID usable by a surgical robotic system to control actuators includes a finger clutch that is easy to reach and actuate by a user. The finger clutch can be mounted at an end of a device housing to be within reach of a finger of the user when the user is holding the UID. The finger clutch may include a conductive pad forming a portion of a capacitive sensor. The capacitive sensor can sense a change in capacitance when the user touches the finger clutch over the conductive pad. A touch is contrasted here with a press because a touch may include substantially zero force application. That is, touching the finger clutch requires less pressure than actuating a button. Thus, the finger clutch can be actuated with zero force to avoid an unintentional movement of a robotic end effector.

Figure 1:
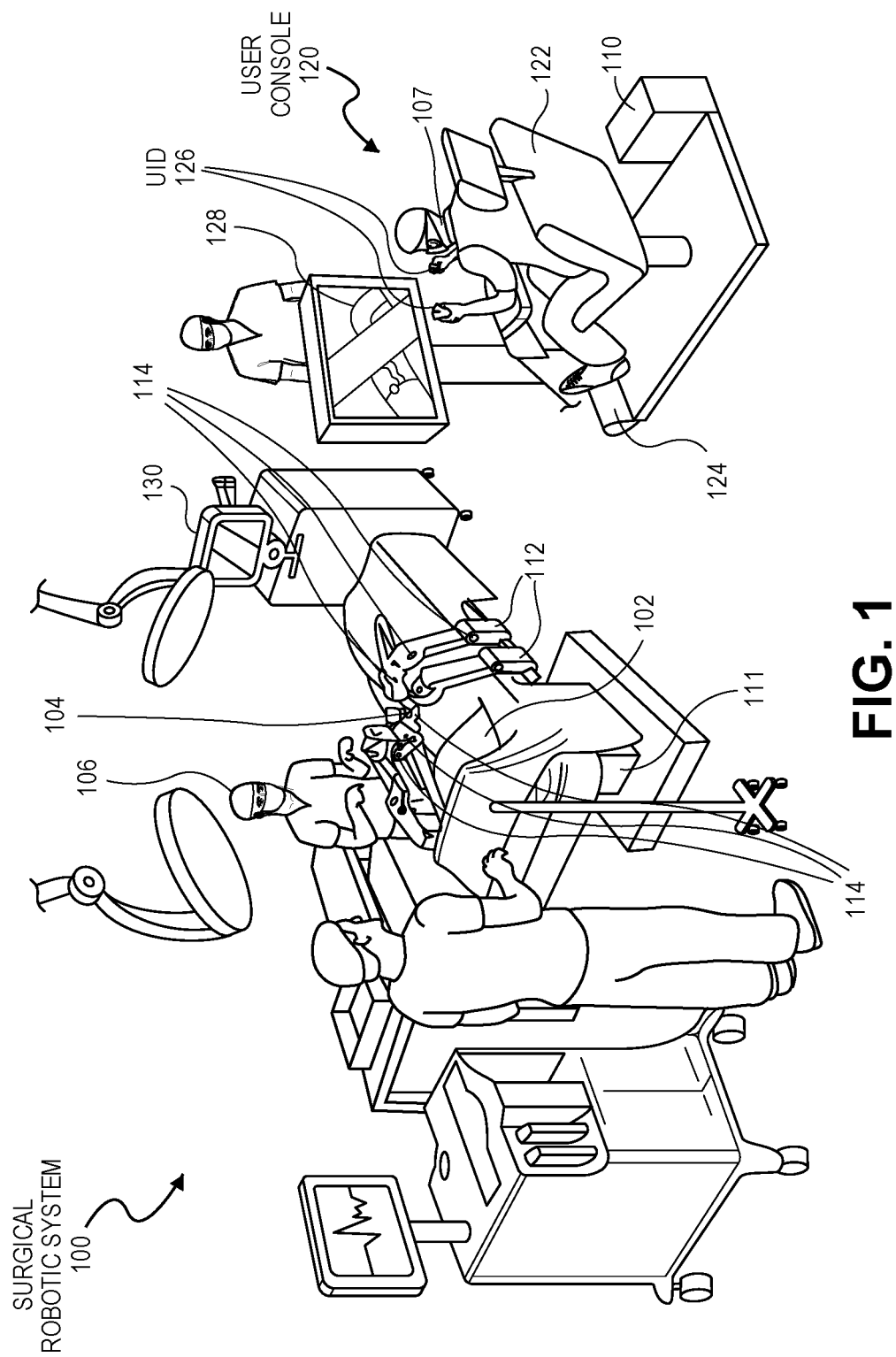
FIG. 1 is a pictorial view of an example surgical robotic system in an operating arena, in accordance with an embodiment.

Referring to FIG. 1, this is a pictorial view of an example surgical robotic system 100 in an operating arena. The surgical robotic system 100 includes a user console 120, a control tower 130, and one or more surgical robotic arms 112 at a surgical robotic platform 111, e.g., a table, a bed, etc. The system 100 can incorporate any number of devices, tools, or accessories used to perform surgery on a patient 102. For example, the system 100 may include one or more surgical tools 104 used to perform surgery. A surgical tool 104 may be attached to a distal end of a surgical robotic arm 112, for executing a surgical procedure.

Each surgical tool 104 may be manipulated manually, robotically, or both, during the surgery. For example, surgical tool 104 may be a tool used to enter, view, or manipulate an internal anatomy of patient 102. In an embodiment, surgical tool 104 includes an end effector, e.g., a grasper that can grasp tissue of patient 102. Surgical tool 104 may be handled manually, by a bedside operator 106; or it may be moved robotically, via actuated movement of the surgical robotic arm 112 to which it is attached. Surgical robotic arms 112 are shown as a table-mounted system, but in other configurations the surgical robotic arms 112 may be mounted in a cart, ceiling or sidewall, or in another suitable structural support.

Generally, a remote operator 107, such as a surgeon or other operator, may use the user console 120 to remotely manipulate the surgical robotic arms 112 and/or surgical tools 104, e.g., by teleoperation. The user console 120 may be located in the same operating room as the rest of the system 100, as shown in FIG. 1. In other environments however, the user console 120 may be located in an adjacent or nearby room, or it may be at a remote location, e.g., in a different building, city, or country. The user console 120 may comprise a seat 122, foot-operated controls 124, one or more handheld user interface devices, UIDS 126, and at least one user display 128 that is configured to display, for example, a view of the surgical site inside patient 102. In the example user console 120, remote operator 107 is sitting in seat 122 and viewing the user display 128 while manipulating a foot-operated control 124 and a handheld UID 126 in order to remotely command movement of the surgical robotic arms 112 and surgical tools 104 (that are mounted on the distal ends of the surgical robotic arms 112). Foot-operated control(s) 124 can be foot pedals, such as seven pedals, that generate motion command signals when actuated. User console 120 may include one or more additional input devices (FIG. 9), such as a keyboard or a joystick, to receive manual inputs to command operations of user console 120, or other components of surgical robotic system 100.

In some variations, bedside operator 106 may also operate system 100 in an "over the bed" mode, in which bedside operator 106 (user) is now at a side of patient 102 and is simultaneously manipulating a robotically-driven tool 104 (attached to surgical robotic arm 112), e.g., with a handheld UID 126 held in one hand, and a manual laparoscopic tool. For example, the bedside operator's left hand may be manipulating the handheld UID 126 to command a robotic component, while the bedside operator's right hand may be manipulating a manual laparoscopic tool. Thus, in these variations, bedside operator 106 may perform both robotic-assisted minimally invasive surgery and manual laparoscopic surgery on patient 102.

During an example procedure (surgery), patient 102 is prepped and draped in a sterile fashion to achieve anesthesia. Initial access to the surgical site may be performed manually while the surgical robotic arms 112 of surgical robotic system 100 are in a stowed configuration or withdrawn configuration (to facilitate access to the surgical site). Once access is completed, initial positioning or preparation of the robotic system including its surgical robotic arms 112 may be performed. Next, the surgery proceeds with the remote operator 107 at the user console 120 utilizing the foot-operated controls 124 and the UIDs 126 to manipulate the various surgical tools, and perhaps an imaging system, to perform the surgery. Manual assistance may also be provided at the procedure bed or table, by sterile-gowned bedside personnel, e.g., bedside operator 106 who may perform tasks such as retracting tissues, performing manual repositioning, and tool exchange upon one or more of the surgical robotic arms 112. Non-sterile personnel may also be present to assist remote operator 107 at the user console 120. When the procedure or surgery is completed, the system 100 and/or user console 120 may be configured or set in a state to facilitate post-operative procedures such as cleaning or sterilization and healthcare record entry or printout via user console 120.

In one embodiment, remote operator 107 holds and moves UID 126 to provide an input command to move one or more actuators 114 in surgical robotic system 100. There may be several sets of actuators corresponding to different robotically-driven portions of the system. For example, a first set of one or more actuators 114 can move joints of surgical robotic arm 112, and a second set of one or more actuators 114 can move components of surgical tool 104, such as an end effector of surgical tool 104. UID 126 may be communicatively coupled to the rest of surgical robotic system 100, e.g., via a computer system 110. UID 126 can generate spatial state signals corresponding to movement of UID 126, e.g., position and orientation of the handheld housing of the UID. The spatial state signals can include at least one pose signal and at least one position signal, and can define a pose and a position of the UID 126 in six degrees of freedom. The spatial state signals may be input signals used by one or more processors of surgical robotic system 100 to control movement of actuators 114. The one or more processors of surgical robotic system 100 may use the spatial state signals, or control signals derived from the spatial state signals, to control proportional motion of actuators 114. In one embodiment, a console processor of computer system 110 receives the spatial state signals and generates the corresponding control signals. The control signals can be further processed by a surgical system processor coupled to the actuators 114 of surgical robotic arm 112 and/or surgical tool 104. Based on these control signals, which control how the actuator 114 is energized to move a segment or link of surgical robotic arm 112, the movement of a corresponding surgical tool 104 that is attached to the surgical robotic arm 112 may mimic the movement of UID 126. Similarly, interaction between remote operator 107 and UID 126 can generate, for example, a grip control signal that causes a grip motion or a grasp motion of an end effector, e.g., a gripping movement by a jaw of a grasping movement by a grasper, of surgical tool 104 to close and grip the tissue of patient 102.

The motion of UID 126 may alternatively be provided to command other operations by surgical robotic system 100. For example, gestures detected by a finger clutch, as described below, may generate a clutch signal to pause the motion of actuators 114 corresponding to the surgical robotic arm 112 and surgical tool 104. For example, when a user touches the finger clutch of UID 126 with a finger, the finger clutch may generate a clutch signal, and the clutch signal may be an input signal to pause all motion of actuators 114, and correspondingly, all motion of surgical robotic arm 112 and surgical tool 104. When all motion of surgical robotic arm 112 and surgical tool 104 are paused, there is no movement in any direction and no change in orientation of surgical robotic arm 112 and surgical tool 104. The clutch signal may be termed a "clutch activation signal" when the assertion of the signal pauses motion of actuators 114. Similarly, the input signal may be a "clutch deactivated signal" when no touch by user 107 is detected, and motion of actuators 114 is not paused. The clutch signal, e.g., the clutch activation signal, when asserted, can pause motion of the robotic arm and surgical tool regardless of the spatial state signals. Accordingly, the clutch signal effectively overrides the actuation command that is derived from the spatial state signals. In an embodiment, one or more capacitive sensing pads may be located on UID 126, and the user may touch the capacitive sensing pads to command a camera view of an endoscope, a cursor on a display of user console 120, etc., while performing a diagnostic, surgical, laparoscopic, or minimally invasive surgical procedure, or another robotic procedure.

Surgical robotic system 100 may include several UIDs 126, where respective control signals are generated for each UID that are used by one or more processors of the surgical robotic system 100 to control actuators 114 of a respective surgical robotic arm 112 and/or surgical tool 104. For example, remote operator 107 may move a first UID 126 to command motion of actuators 114 that are in a left surgical robotic arm, where the actuator responds by moving linkages, gears, etc., in that surgical robotic arm 112. Similarly, movement of a second UID 126 by remote operator 107 commands motion of other actuators 114, which in turn move other linkages, gears, etc., of the surgical robotic system 100. Surgical robotic system 100 may include a right surgical robotic arm 112 that is secured to the bed or table to the right side of the patient, and a left surgical robotic arm 112 that is at the left side of the patient. Each surgical robotic arm 112 can have several joints, and movement of the joints can be actuated by one or more corresponding actuators 114. For example, each actuator 114 may include one or more motors that are controlled by the one or more processors of surgical robotic system 100 so that they drive the rotation of a joint of surgical robotic arm 112 or surgical tool 104. Movement of the joints causes movement of the links or segments of the arm or tool, which can change, for example, relative to the patient, an orientation of an endoscope or a grasper of surgical tool 104 that is attached to that surgical robotic arm 112. The spatial state signals generated from a particular UID 126 can be used by the one or more processors of surgical robotic system 100 to control motion of several actuators 114 in the same surgical robotic arm 112. Input signals generated by UIDs 126 can also be used to control motion of respective surgical tool graspers. For example, each UID 126 can generate a respective grip signal that the one or more processors can use to control motion of an actuator, e.g., a linear actuator, that opens or closes jaws of the grasper at a distal end of the surgical tool to grip tissue within patient 102.

In some aspects, the communication between platform 111 and user console 120 may be through a control tower 130, which may translate input signals that are received from user console 120 (and more particularly from computer system 110) into output signals that are transmitted to surgical robotic arms 112 and surgical tools 104 on robotic platform 111. The control tower 130 may also transmit status and feedback from platform 111 back to user console 120. The communication connections between the robotic platform 111, user console 120, and control tower 130 may be via wired and/or wireless links, using any suitable ones of a variety of data communication protocols. Any wired connections may be optionally built into the floor and/or walls or ceiling of the operating room. Surgical robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

It will be appreciated that the operating room scene in FIG. 1 is illustrative and may not accurately represent certain medical practices.

Figure 2:
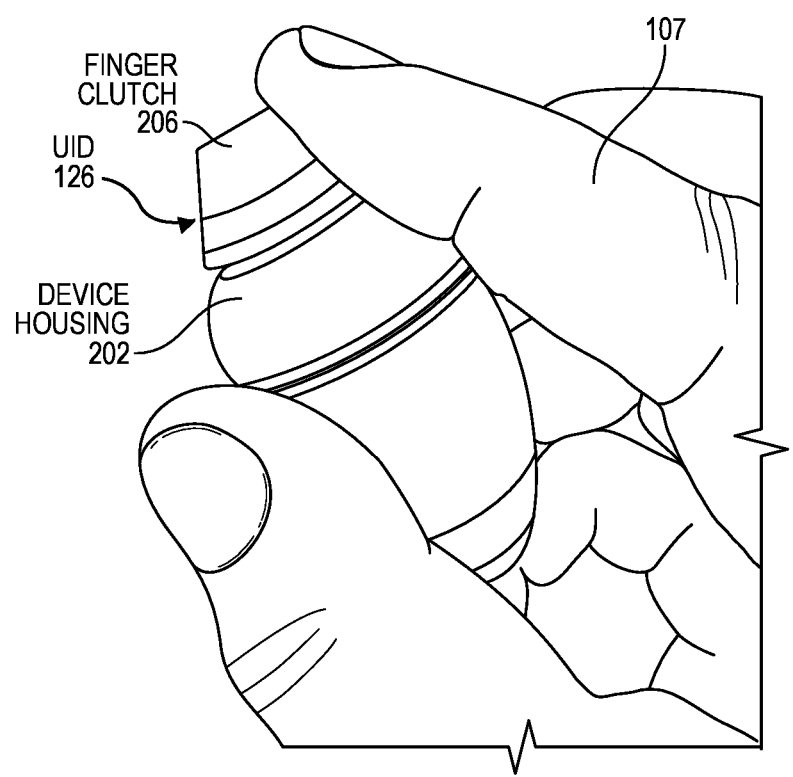
FIG. 2 is a pictorial view of a user interface device having a finger clutch, in accordance with an embodiment.

Referring to FIG. 2, a pictorial view of a UID having a finger clutch is shown in accordance with an embodiment. A UID 126 can include a device housing 202 to be held by a user 107. For example, user 107 may hold device housing 202 between several fingers and move UID 126 within a workspace. The workspace may be a range of reach of user 107. As described below, UID 126 may include a tracking sensor to detect a position and/or orientation of device housing 202 when user 107 moves the UID 126, and the detected position and/or orientation may be correlated to another component of a surgical robotic system. For example, the tracking sensor may detect translation, rotation, or tilting of device housing 202 within the workspace. The tracking sensor may include an accelerometer and/or a gyroscope or other inertial sensors. The movement of UID 126 within the workspace can cause a corresponding movement of a surgical robotic arm, a surgical tool, or an end effector of the surgical tool, e.g., a grasper or a jaw, of the surgical robotic system.

UID 126 may include a clutch mechanism to decouple movement of UID 126 from movement of the surgical robotic arm 112 and/or surgical tool 104. For example, UID 126 can include a finger clutch 206 mounted on device housing 202 to clutch the surgical robotic system. Finger clutch 206 may be so-termed because it may be actuated by a touch from a finger of user 107. That is, when user 107 touches finger clutch 206 with the finger, the touch may be detected as a clutch input. In response to the clutch input, movement of UID 126 detected by the tracking sensor may not be used by the one or more processors to control movement of the surgical robotic system. When the clutch input is removed (when the touch is ended) the movement of UID 126 may again cause a corresponding movement of the surgical robotic system. That is, when finger clutch 206 is unclutched, e.g., by removing the finger from finger clutch 206, UID 126 movement may again be detected and used by surgical robotic system 100 as a motion control input.

The clutching mechanism of UID 126 can allow user 107 to reposition UID 126 within the workspace when a limit of the workspace has been reached. For example, by extending an arm fully from a start position in a direction while holding UID 126, user 107 may reach the limit of the workspace, e.g., an edge of the workspace. To reposition UID 126 within the workspace and allow for additional movement in the direction of the workspace edge, user 107 can touch finger clutch 206 with an index finger to disconnect the robotic system from the movement of UID 126. User 107 may then move UID 126 back to the start position within the workspace and unclutch the surgical robotic system 100 by lifting the index finger from finger clutch 206. Additional movement in the first direction may then be performed by moving UID 126 to command movement of surgical robotic arm 112.

Figure 3:
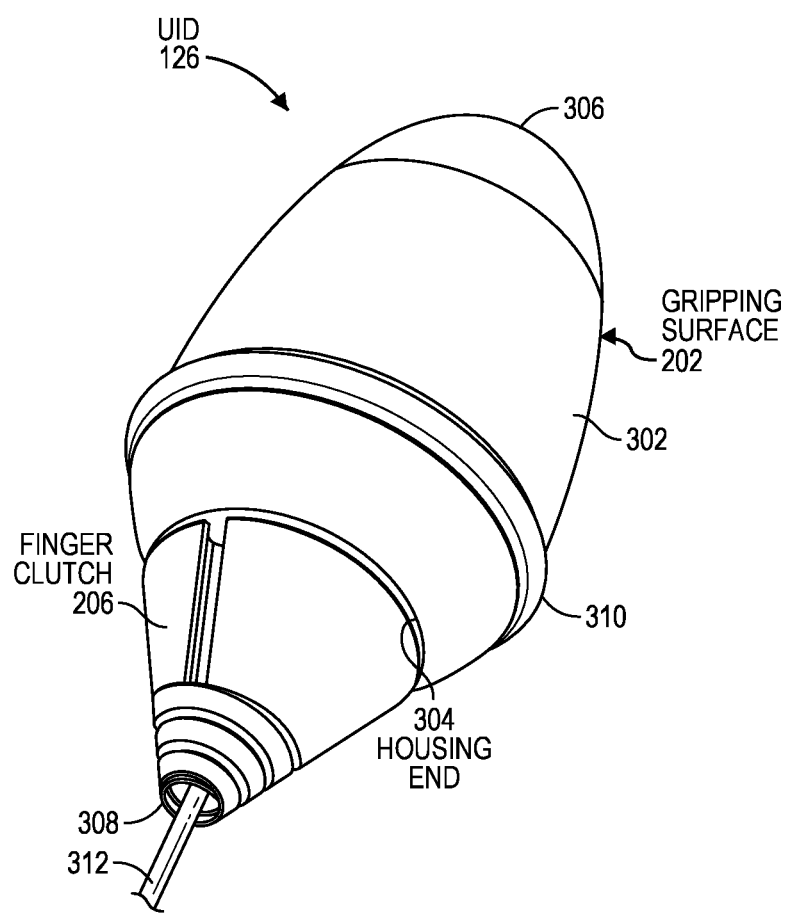
FIG. 3 is a perspective view of a user interface device, in accordance with an embodiment.

Referring to FIG. 3, a perspective view of a UID is shown in accordance with an embodiment. UID 126, which is handled by remote operator 107 to command movement of surgical tool 104 and/or surgical robotic arm 112, can be a radially-symmetric device to enable or pause teleoperation of the commanded portion of surgical robotic system 100. More particularly, device housing 202 of UID 126 can include a gripping surface 302 to be held between several fingers of user 107. Device housing 202 can have one or more rounded or bulbous surface contours. For example, device housing 202 may be generally ovoid or egg-shaped, or it may be a ellipsoid. In an embodiment, a portion of device housing 202 in front of a circumferential ridge 310 of device housing 202 may be shorter and have a less gradual contour or taper than a portion of device housing 202 in back of ridge 310. Thus, the distal portion and the proximal portion of device housing 202 may have different radii of curvatures measured from a point where a longitudinal axis of UID 126 intersects a transverse plane on which ridge 310 is located.

In an embodiment, finger clutch 206 is mounted on a housing end 304. For example, housing end 304 may be a distal end of the device housing 202. Housing end 304 can be a location or surface that is at an extremity of housing 202 in a first longitudinal direction. For example, the location can be an edge of housing 202 that is farthest from an opposite end of housing, e.g., a proximal end 306.

Finger clutch 206 may extend distally from housing end 304. Locating finger clutch 206 at a front part of UID 126 may allow user 107 to easily reach forward and touch finger clutch 206 with an index finger while holding gripping surface 302 between a thumb and another finger. Accordingly, UID 126 may be sized and shaped to be comfortably held within a hand of user 107. In an embodiment, a longitudinal distance between proximal end 306 of device housing 202 and a distal tip 308 of UID 126 may be less than 3 inches, e.g., in a range of 1-2 inches. Similarly, a maximum diameter, e.g., a diameter of ridge 310, of device housing 202 in a direction transverse to the longitudinal distance between proximal end 306 and distal tip 308 may be less than 3 inches, e.g., in a range of 1-2 inches. In an embodiment, the longitudinal distance of UID 126 may be greater than the maximum diameter of device housing 202.

Command signals input through UID 126 may be communicated to computer system 110 through a wired or wireless connection. In an embodiment, an electrical wire 312 extends from distal tip 308 of UID 126 to connect UID 126 to computer system 110. Electrical wire 312 may provide power to UID 126 and may carry sensor signals, e.g., tracking sensor signals or clutch signals, to computer system 110. Accordingly, UID 126 may be a peripheral device used to input commands to computer system 110. UIDs 126 can be used in combination with other peripheral input devices. For example, a foot pedal switch may be connected to computer system 110 to provide a clutch input to surgical robotic system 100. Whereas each UID 126 may be individually clutched to pause teleoperation of respective surgical robotic arms or surgical tools, the respective surgical robotic arms or tools may be clutched at a same time by pressing the foot pedal switch. Thus, movement of actuators 114 may be commanded by UIDs 126 and other peripheral input devices of computer system 110.

Figure 4:
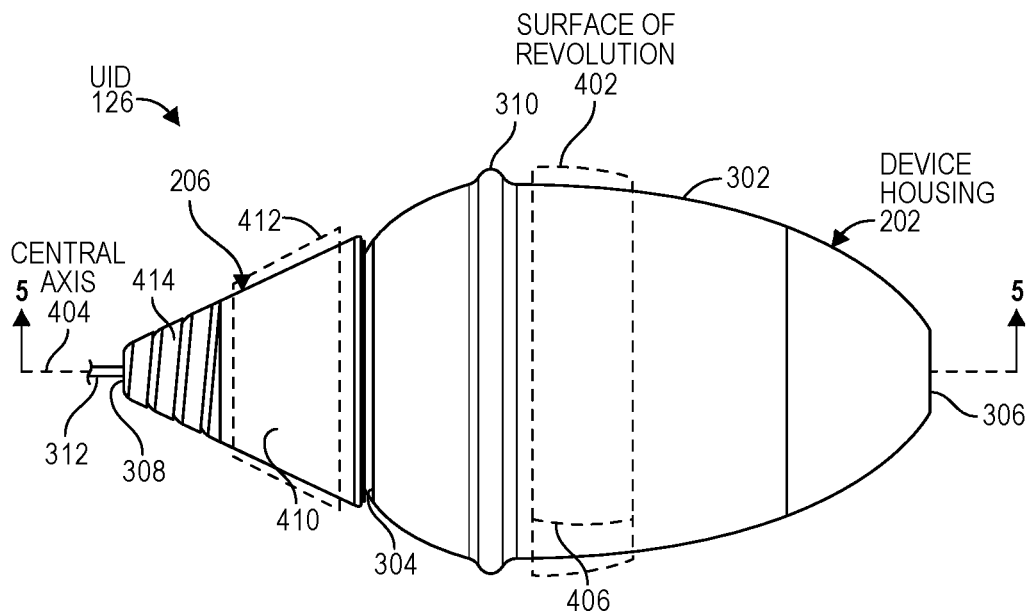
FIG. 4 is a side view of a user interface device, in accordance with an embodiment.

Referring to FIG. 4, a side view of a UID is shown in accordance with an embodiment. Gripping surface 302 of UID 126 can include a surface of revolution 402 about a central axis 404. Central axis 404 can extend longitudinally through UID 126 from proximal end 306 to distal tip 308. Accordingly, gripping surface 302 may be an outer surface of UID 126 between housing end 304 and proximal end 306.

Central axis 404 may be an axis of symmetry. That is, surface of revolution 402 may include a gripping surface contour 406 revolved about central axis 404 such that the revolved surface is radially-symmetric about central axis 404. Gripping surface 302 is shown as a dashed region proximal to ridge 310, however, gripping surface 302 may extend an entire distance between housing end 304 and proximal end 306. That is, gripping surface contour 406 is shown as a curvilinear line segment extending over a portion of device housing 202, however, gripping surface contour 406 may extend over gripping surface 302 from proximal end 306 to housing end 304. When gripping surface contour 406 is revolved about central axis 404, surface of revolution 402 is formed having radially symmetric features. For example, ridge 310 may be a raised ring extending circumferentially around device housing 202 at a longitudinal location between housing end 304 and proximal end 306.

The radial symmetry of device housing 202 can allow user 107 to comfortably rotate UID 126 about central axis 404. For example, user 107 may roll device housing 202 between fingers to generate input command signals that are processed to control a twisting motion of a surgical tool mounted on a surgical robotic arm. Furthermore, the radial symmetry of UID 126 enables user 107 to grasp device housing 202 at any position about central axis 404. Accordingly, user 107 may access and manipulate UID 126 comfortably.

Finger clutch 206 may also be radially symmetric about central axis 404. In an embodiment, finger clutch 206 includes a clutch cover 410 having a second surface of revolution 412 about central axis 404. For example, second surface of revolution 412 may be a frustoconical surface tapering from a larger diameter at housing end 304 to a smaller diameter nearer to distal tip 308. The frustoconical surface can have a cone shape with a tip of the cone shape removed. The diameter may change continuously over a length of clutch cover 410. The tapering surface can be accessible to a user 107 regardless of how device housing 202 is gripped. That is, a contour of second surface of revolution 412 may be identical at all radial positions about central axis 404 such that clutch cover 410 has a consistent feel to user 107 regardless of where user 107 touches clutch cover 410.

The frustoconical surface of clutch cover 410 is provided by way of example, and not limitation. Clutch cover 410 may incorporate a different shape. For example, clutch cover 410 may be formed as shown in any of the embodiments of FIGS. 8A-8E.

Finger clutch 206 may include a strain relief 414 extending from clutch cover 410 to distal tip 308. Strain relief 414 can be an elastomeric component having a conical shape and a central bore through which electrical wire 312 may enter UID 126. More particularly, strain relief 414 may support electrical wire 312 extending distally from distal tip 308 of UID 126. Accordingly, strain relief 414 may relieve lateral loads placed on electrical wire 312. Strain relief 414 may not be needed in an embodiment. For example, when UID 126 does not include electrical wire 312, e.g., when UID 126 communicates wirelessly with computer system 110, strain relief 414 may be omitted. In such case, finger clutch 206 may have a conical outer shape, rather than a frustoconical outer shape.

Figure 5:
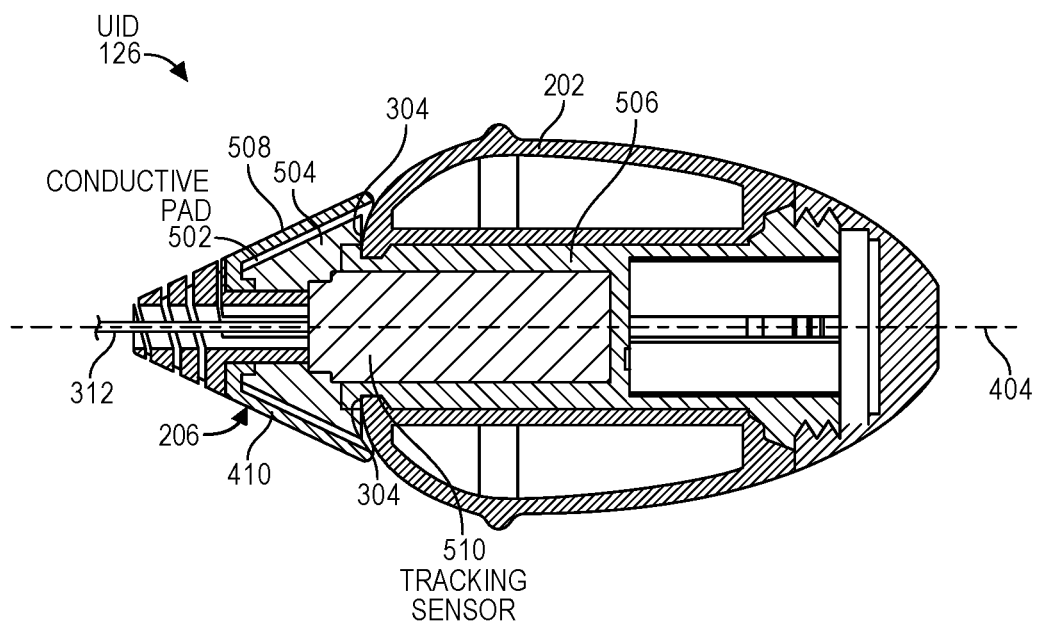
FIG. 5 is a sectional view, taken about line 5-5 of FIG. 4, of a user interface device, in accordance with an embodiment.

Referring to FIG. 5, a sectional view, taken about line 5-5 of FIG. 4, of a UID is shown in accordance with an embodiment. Clutch cover 410 of finger clutch 206 may be mounted over a conductive pad 502. Conductive pad 502 may extend around central axis 404. For example, whereas central axis 404 may extend longitudinally, an outer surface of conductive pad 502 may follow a path along a transverse plane orthogonal to longitudinal axis 404. The path may extend fully around central axis 404, e.g., the profile on the transverse plane may be circular. Alternatively, the path may extend partially around central axis 404, e.g., the profile may be c-shaped. In an embodiment, the profile sweeps over an angle of at least 270 degrees, where the angle is measured about central axis 404. The profile described above may be a singular transverse slice of conductive pad 502, and in an embodiment, a shape of the profile may be the same over a length of conductive pad 502. That is, each transverse slice of conductive pad 502 taken along the length of conductive pad 502 may be a same shape, e.g., circular.

Conductive pad 502 may be a band of conductive material conforming to an interior surface of clutch cover 410. Conductive pad 502 may include a ring of conductive film having a frustoconical shape. Conductive pad 502 may be continuous or discontinuous around central axis 404. For example, a longitudinal slit may be formed through conductive pad 502 such that conductive pad 502 extends only partially around central axis 404. Accordingly, conductive pad 502 may have a c-shaped transverse cross-section. Alternatively, conductive pad 502 may extend fully around central axis 404. Accordingly, conductive pad 502 may have an annular transverse cross-section. Although not shown, in one embodiment, a wire may join conductive pad 502 at one end to an input of a sensing amplifier circuit (viewed as part of a UID processor within the device housing 202) at another end, wherein the sensing amplifier circuit may produce a sensed signal that changes in accordance with the signal on the wire, which changes as a result of the capacitance of the conductive pad 502 changing, based on proximity of the user's finger to the conductive pad 502 or based on the touch of the user's finger on the conductive pad 502. A device processor in the housing 202 (UID processor 606—see FIG. 6) may process a digitized version of a sensed signal to determine whether or not a capacitance change has occurred at the conductive pad 502.

Finger clutch 206 may include a pad mount 504 fixed to housing end 304. For example, device housing 202 may be mounted on a UID body 506 extending longitudinally along central axis 404. UID body 506 may have a distal end extending distal to housing end 304. In an embodiment, pad mount 504 is attached to the distal end of UID body 506, and thus, pad mount 504 is fixed relative to housing end 304.

In an embodiment, pad mount 504 is radially symmetric about central axis 404. For example, pad mount 504 may include an outer surface, e.g., a pad surface (FIG. 6), that extends around central axis 404. The pad surface can be a surface of revolution having a conical or frustoconical shape. The shape of the pad surface may be the same as an outer touch surface 508 of clutch cover 410. Accordingly, a radial distance between outer touch surface 508 and the pad surface may be the same over a length of pad mount 504. Alternatively, the radial distance may vary over the length. For example, outer touch surface 508 can be frustoconical and the pad surface can be cylindrical, and thus, a distance between the surfaces may be less at a distal end of pad mount 504 than at a proximal end of pad mount 504.

Conductive pad 502 can be mounted on pad mount 504. For example, conductive pad 502 may be joined to pad mount 504. More particularly, conductive pad 502 may be located between an outer surface of pad mount 504 and an interior surface of clutch cover 410. By contrast, clutch cover 410 may include outer touch surface 508 facing outward toward a surrounding environment. When a finger of user 107 touches outer touch surface 508 of clutch cover 410, the finger is separated from conductive pad 502 by a wall thickness of clutch cover 410. Clutch cover 410 can be formed from a dielectric material, e.g., a plastic, and thus, a capacitance across the wall of clutch cover 410 will change when the conductive finger of user 107 touches outer touch surface 508. A thickness of the wall may be limited to ensure that the change in capacitance is detectable. For example, the wall thickness of clutch cover 410 between the interior surface and outer touch surface 508 may be less than 1 mm. Accordingly, clutch cover 410 and conductive pad 502 provide a capacitive sensor on central axis 404 at housing end 304. The capacitive sensor extends around central axis 404.

UID 126 may include other sensors. For example, UID 126 may include a tracking sensor 510 mounted within device housing 202. More particularly, tracking sensor 510 may be mounted within UID body 506. UID body 506 can include a cylindrical bore within which tracking sensor 510 is sized to fit in a sliding or press fit.

Tracking sensor 510 can be configured to generate one or more spatial state signals in response to movement of device housing 202. The spatial state signals may correspond to a position and/or orientation of UID 126 in free space. The spatial state signals can be processed to control a motion of surgical robotic arm 112. For example, when user 107 moves UID 126 rightward within the workspace, a surgical tool mounted on the surgical robotic arm may be controlled by one or more processors of the system to move rightward also. Similarly, rotating UID 126 about central axis 404 may cause the surgical tool, or an end effector of the surgical tool, to similarly rotate in space about a corresponding longitudinal axis.

Tracking sensor 510 may include an accelerometer, a gyroscope, a magnetometer, or one or more other transducers capable of converting physical movement into a corresponding electrical signal. For example, tracking sensor 510 may include a magnetic tracking probe capable of measuring six degrees of freedom, including physical displacement or translation in one or more directions (e.g., in XYZ space or another suitable coordinate system), roll, pitch, and yaw (e.g., rotation about one or more axes or tilting relative to one or more axes) of UID 126. In an embodiment, several tracking sensors 510 are used to provide redundancy in position and/or orientation detection of UID 126. The tracking sensor(s) 510 can output electrical signal(s), and the electrical signal(s) can be combined, e.g., averaged, into the spatial state signals. The spatial state signals may be used by the processor(s) of system 100 to cause motion of surgical robotic arm 112 and/or surgical tool 104.

Tracking sensor 510 may additionally or alternatively include other types of sensors for tracking position and/or orientation of UID 126. For example, tracking sensor 510 may include one or more gyrosocopes, accelerometers, and/or magnetometers, some of which may be part of an inertial measurement unit (IMU). These and other suitable sensors may be disposed on a printed circuit board in or on device housing 202 of UID 126.

It is noted that, although UID 126 has been described as having surfaces of revolution and/or radially symmetric features about central axis 404, this does not imply that the components of UID 126 are formed by a turning process. For example, the components of UID 126 having outward facing surfaces may be manufactured using injection molding processes. The molding processes may utilize molds having radially symmetric contours to form the surfaces as described above.

Figure 6:
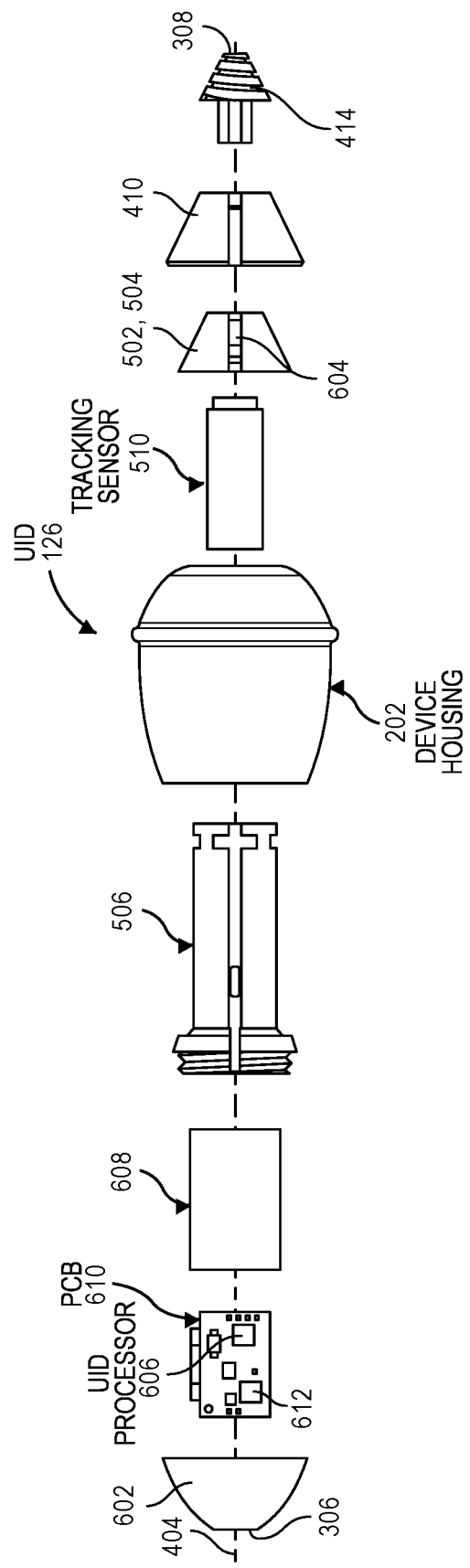
FIG. 6 is an exploded view of a user interface device, in accordance with an embodiment.

Referring to FIG. 6, an exploded view of a UID is shown in accordance with an embodiment. The components of UID 126 can be spread along central axis 404 between a cap 602 at a proximal end 306 of UID 126 and strain relief 414 at a distal tip 308 of UID 126. More particularly, proximal end 306 of UID 126 may be on cap 602, and distal tip 308 of UID 126 may be on strain relief 414. UID body 506, device housing 202, tracking sensor 510, conductive pad 502, pad mount 504, and clutch cover 410 are similarly distributed along central axis 404 in the exploded view. In an embodiment, conductive pad 502 wraps around a portion of pad mount 504. More particularly, pad mount 504 includes a pad surface 604 visible through a longitudinal slot formed between circumferential ends of conductive pad 502. Conductive pad 502 may be mounted on pad mount 504 between pad surface 604 and an interior surface of clutch cover 410.

Device housing 202 may be formed at least partially of a flexible material such as silicone, latex, or another suitable polymer or alloy. The housing material may be a medical grade material, and may be sterilizable, e.g., by autoclave, solvent wipe-down, etc. Device housing 202 may be removable from the rest of UID 126 for disposal.

UID body 506 may have a cylindrical shape. UID body 506 may be disposed along central axis 404 within device housing 202. Accordingly, tracking sensor 510 may be disposed within device housing 202, e.g., mounted within UID body 506, and can be positioned on central axis 404. Tracking sensor 510 may detect translation, rotation, or tilting of device housing 202 relative to central axis 404.

UID 126 may include an internal volume to receive various electronics and/or other components. For example, UID 126 may include a UID processor 606 mounted within device housing 202. The UID processor 606 may encompass circuitry for analog and digital signal processing, including sensing amplifier circuits and analog to digital conversion circuitry used to interface with the capacitive sensor, and logic circuitry including programmable logic or a programmable digital processor. UID processor 606 may be mounted on a printed circuit board 610 having various sensor terminals to connect UID processor 606 to device sensors, e.g., finger clutch 206 or tracking sensor 510. A battery 612 may be mounted on the printed circuit board 610 to power electronic components of UID 126. UID processor 606 may be received within a wall of UID body 506 such that the processor and electrical connection on the printed circuit board 610 are protected against physical impacts.

Electrical wire 312 (not shown) may extend along central axis 404 through central bores of each component of UID 126 to connect to UID processor 606. For example, electrical wire 312 may extend along central axis 404 through strain relief 414, pad mount 504, tracking sensor 510, and UID body 506 to attach to a terminal on UID processor 606 or printed circuit board 610. UID processor 606 may also be electrically connected to conductive pad 502. For example, a wire may be joined to UID processor 606 at one end and joined to conductive pad 502 at another end. The wire, which may be a different electrical connector than electrical wire 312, may therefore extend between UID processor 606 or printed circuit board 610 and conductive pad 502. A first end of the wire may be attached to a terminal on UID processor 606 or printed circuit board 610, and a second end of the wire may be attached to conductive pad 502. The wire may conduct a capacitance signal to UID processor 606 that may be compared to a ground terminal. The ground terminal may be on UID processor 606 or printed circuit board 610. Accordingly, UID processor 606 may be configured to detect and/or measure a magnitude and/or change of capacitance of conductive pad 502 based on the capacitance signal received through the wire from conductive pad 502.

UID 126 may include other circuitry. By way of example, UID 126 can include a drop detection sensor in device housing 202. For safety reasons, an interlock may be used to prevent unintentional instrument movement when UID 126 is dropped. For example, the drop detection sensor can generate a drop signal in response to entering a free fall state when dropped. In an embodiment, the drop detection sensor is a tracking sensor (FIG. 5), which monitors movement of UID 126. When the tracking sensor detects movement corresponding to a dropped state, the sensor generates a clutch signal to pause all motion of surgical robotic system 100.

In an embodiment, UID 126 includes a gripping sensor 608 in device housing 202. In an embodiment, gripping sensor 608, when squeezed, generates a grip signal. More particularly, gripping sensor 608 is configured to generate a grip signal in response to a squeeze on device housing 202. Accordingly, gripping sensor 608 can detect when user 107 squeezes device housing 202. The detected squeeze may be a seventh degree of freedom sensation by UID 126, in addition to the six degrees of freedom detected by tracking sensor 510. More particularly, an end effector, such as a grasper, of surgical tool 104 can have a pose and position in space that changes in response to an orientation signal from the tracking sensor, and a gripping configuration that changes in response to the grip signal from gripping sensor 608. The grip signal can cause motion of an actuator of surgical robotic system 100 to change the gripping configuration. For example, the end effector of surgical tool 104 may include fingers that simulate movement of fingers of operator 107. When operator 107 squeezes device housing 202, gripping sensor 608 can generate the grip signal to cause the grasper to close. When operator 107 releases device housing (or squeezes less), the grip signal can change to cause the grasper to open. Accordingly, surgical robotic system 100 can include an actuator 114 that moves the end effector, e.g., the grasper, of surgical tool 104 based on the grip signal.

Gripping sensor 608 can measure the opening and/or closing of the fingers of operator 107. Gripping sensor 608 can be a grip flex circuit. The grip flex circuit may be a printed circuit wrapped around an outer surface of UID body 506. The grip flex circuit can detect when user 107 squeezes device housing 202. Device housing 202 may be formed from a compliant material, such as silicone, to be resilient under the squeeze of the user 107. User 107 may squeeze device housing 202 as an input command to cause movement of surgical robotic arm 112 or surgical tool 104. When user 107 squeezes device housing 202, device housing 202 can deform grip flex circuit 608 and the physical deformation may be converted into an electrical signal, e.g., a capacitance signal. The electrical signal may be transmitted to UID processor 606, which may have onboard analog and digital electronics to process the electrical signal to detect the squeeze and output a control signal, e.g., the grip signal, corresponding to the user input. One or more processors of system 100 can receive and process the grip signal to control movement of surgical tool 104. Accordingly, the squeeze by user 107 may cause an end effector of the surgical robotic arm, e.g., a grasper, to pinch.

Gripping sensor 608 can detect a change in capacitance representing the squeeze, or may include a proximity sensor to detect proximity (or change in distance) to an inner wall of device housing 202 by other means. Gripping sensor 608 may include any suitable type of proximity sensor for detecting the change in proximity. For example, gripping sensor 608 may include an optical sensor that emits and/or detects returned electromagnetic radiation, e.g., infrared radiation. In another example, gripping sensor 608 may include a capacitive sensor, an ultrasonic sensor, a magnetic sensor, an inductive sensor, or other suitable kind of proximity sensor.

In a variation, UID 126 may include at least one squeeze sensor in the form of a capacitive sensor configured to detect a touch between device housing 202 and the hand of the user holding the housing. For example, a capacitive sensor pad may be disposed on an external surface of UID body 506 and configured to detect hand-based squeezing of the housing by measuring proximity (or change in distance) between the hand of the user holding housing 202 and UID body 506. Alternatively, the capacitive sensor may be disposed on an inner wall of housing 202, or another suitable fixed reference point in UID 126.

The components illustrated in FIG. 6 may be replaced by other similar components. For example, in an embodiment, the capacitive sensor of finger clutch 206 may have any of the structures described below with respect to FIGS. 7A-7C. Similarly, other components of FIG. 6 may be replaced with another embodiment shown in other figures.

Figure 7A:
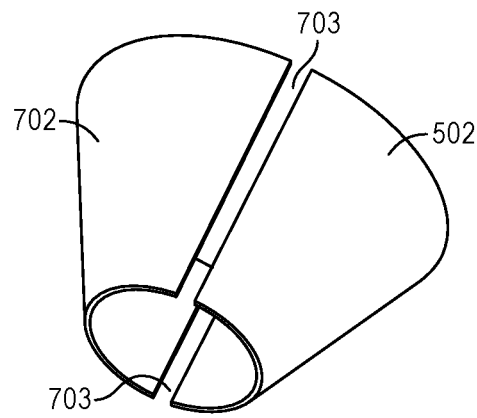
FIGS. 7A-7C are perspective views of a conductive pad of a finger clutch of a user interface device, in accordance with several embodiments.

Referring to FIG. 7A, a perspective view of a conductive pad of a UID 126 is shown in accordance with an embodiment. The capacitive sensor of finger clutch 206 may include several capacitive pads. For example, finger clutch 206 may include conductive pad 502 and a second conductive pad 702 mounted on pad mount 504. Each conductive pad 502 may be a conductive tape wrapped around a portion of pad mount 504. The conductive tape may be a copper tape. The first conductive pad 502 may be a conductive tape wrapped around a portion, e.g., half, of pad surface 604, and second conductive pad 702 may be a conductive tape wrapped around another portion, e.g., a second half of pad surface 604. Accordingly, each conductive pad may have a shape of a segment of a frustoconical shape. The segment may be a portion circumferentially between two longitudinal planes that intersect along central axis 404. The conductive pads 502, 702 may be separated from each other by longitudinal gaps 703 extending between adjacent circumferential edges of the conductive tape segments.

Figure 7B:
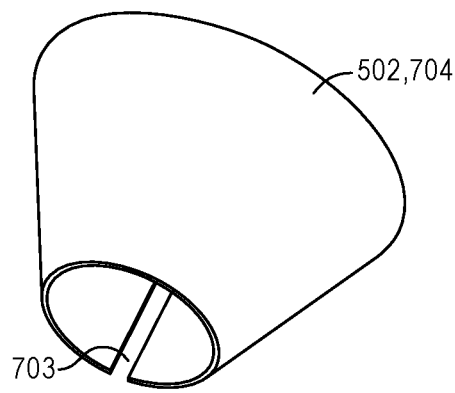

Referring to FIG. 7B, a perspective view of a conductive pad 502 of a UID 126 is shown in accordance with an embodiment. Conductive pad 502 may be a conductive film 704. For example, conductive film 704 may be a thin sheet of aluminum. Conductive film 704 may be wrapped around pad surface 604. The film may wrap entirely around pad surface 604 such that one circumferential end of the film overlaps another circumferential end of the film. Alternatively, the circumferential ends may be separated by a longitudinal gap 703, as shown in FIG. 7B.

Figure 7C:
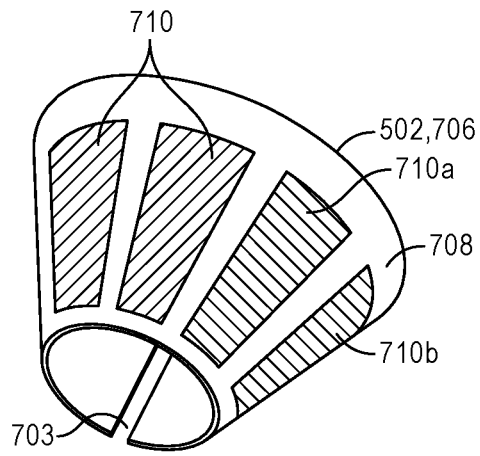

Referring to FIG. 7C, a perspective view of a conductive pad 502 of a UID 126 is shown in accordance with an embodiment. Conductive pad 502 may be a flex circuit 706 mounted on pad mount 504. Flex circuit 706 can include a non-conductive polymer substrate 708, and several printed pads 710 (conductive) may be disposed on polymer substrate 708. Printed pads 710 may be regions formed by patterning a conductive material, e.g., copper, on an outer surface of polymer substrate 708. Accordingly, several printed pads 710 may provide distinct conductive regions along an outer surface of flex circuit 706. Each printed pad 710 may be individually sensed by UID processor 606. For example, a respective wire or electrical trace may extend between each pad and a respective terminal of a sensing amplifier circuit (not shown) of the UID processor 606. Dividing conductive pad 502 into several electrically isolated regions as shown in FIG. 7C may allow UID 126 to detect input gestures such as swiping, e.g., a swipe gesture. More particularly, when user 107 swipes over outer touch surface 508 of finger clutch 206, a change in capacitance may be sequentially sensed at a first printed pad 710a and then at a second printed pad 710b adjacent to the first printed pad 710a. For example, UID processor 606 may be configured to detect a sequence of changes in respective capacitances of first conductive pad 710a and second conductive pad 710b. The sequential change in capacitance can be detected as a swipe gesture over the array of pads. The swipe gesture may be a command to cause a surgical robotic arm to perform a predetermined operation.

Finger clutch 206 may be located such that the capacitive sensor does not interfere with normal use of UID 126. For example, the capacitive sensor may be mounted on the distal end of UID 126 beyond gripping surface 302 where user 107 normally holds UID 126. Alternatively, finger clutch 206 may be mounted on a proximal end of device housing 202, e.g., at proximal end 306 on cap 602. In any case, finger clutch 206 may be within reach of an extended finger of user 107. An outer surface of finger clutch 206 may be shaped to reduce the likelihood of accidental contact between the fingers of user 107 and outer touch surface 508 of finger clutch 206. Several finger clutch 206 shapes and configurations are described below.

Figure 8A:
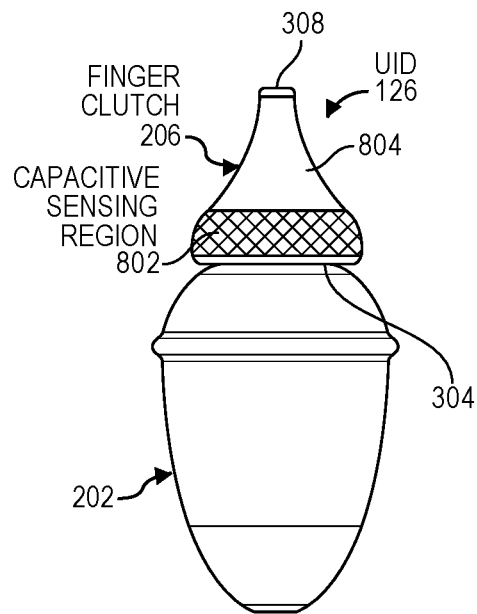
FIGS. 8A-8E are side views of user interface devices having various finger clutch shapes, in accordance with several embodiments.

Referring to FIG. 8A, a side view of a UID 126 having an alternative finger clutch shape is shown. In an embodiment, UID 126 includes device housing 202 having a radially symmetric profile, as described above. Finger clutch 206 of UID 126 may also have a radially symmetric profile. In an embodiment, finger clutch 206 includes a capacitive sensing region 802 and a non-sensing region 804. Capacitive sensing region 802 may be a portion of finger clutch having an underlying conductive pad 502. In FIGS. 8A-8E, capacitive sensing region 802 is illustrated by cross-hatch filler marks and non-sensing region 804 is illustrated by having no filler marks.

Second surface of revolution 412 of finger clutch 206 may have a longitudinal contour extending from housing end 304 to distal tip 308 along a curvilinear path. A radius of second surface of revolution 412 about central axis 404 may continuously reduce in a distal direction, such that a diameter of finger clutch 206 is largest at housing end 304 and is smallest at distal tip 308. The curvilinear path extending over second surface of revolution 412 may be convex outward near housing end 304, and concave inward near distal tip 308. In an embodiment, capacitive sensing region 802 covers a portion of finger clutch 206 adjacent to housing end 304. For example, capacitive sensing region 802 may extend over the convex outward portion of the outer surface of clutch cover 410. The convex outward portion may extend no more than half of a length of finger clutch 206 between housing end 304 and distal tip 308. By contrast, non-sensing region 804 of finger clutch 206 may extend over the concave inward portion of finger clutch 206. The shape of finger clutch 206 shown in FIG. 8A can allow user 107 to rest an extended finger at distal tip 308 while moving surgical robotic arm 112, and then to retract the extended finger to touch capacitive sensing region 802 to pause motion of surgical robotic arm 112.

Figure 8B:
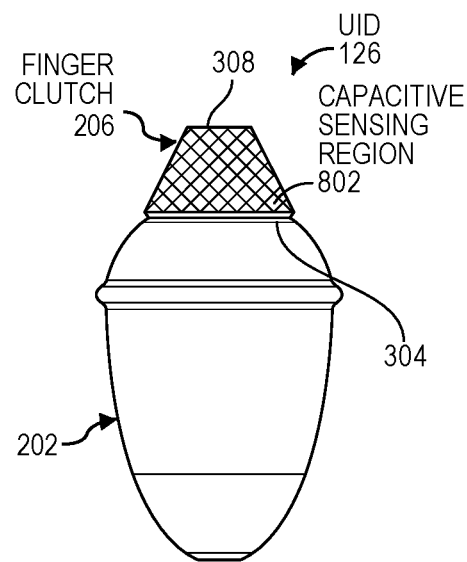

Referring to FIG. 8B, a side view of a UIDs 126 having an alternative finger clutch shape is shown in an embodiment, capacitive sensing region 802 covers an entire outer surface of finger clutch 206. In an embodiment, finger clutch 206 has a frustoconical profile between housing end 304 and distal tip 308. The frustoconical second surface of revolution 412 may have a radius that decreases linearly from housing end 304 to distal tip 308. The shape of finger clutch 206 shown in FIG. 8B can allow user 107 to touch any location on finger clutch 206 to pause motion of surgical robotic arm 112.

Figure 8C:
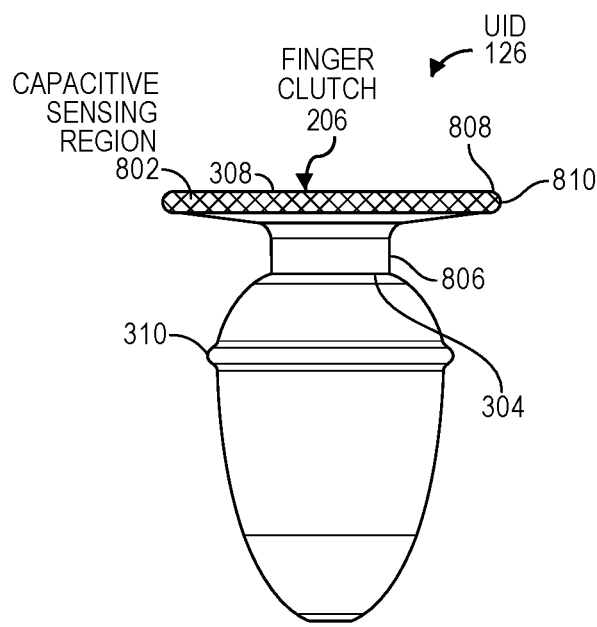

Referring to FIG. 8C, a side view of a UID 126 having an alternative finger clutch shape is shown. In an embodiment, finger clutch 206 includes a cylindrical hub 806 near housing end 304 and a disc portion 808 at distal tip 308. Cylindrical hub 806 may have a constant radius about central axis 404 over a length between housing end 304 and disc portion 808. Similarly, disc portion 808 may have a constant radius about central axis 404 over a length between cylindrical hub 806 and distal tip 308. As shown, transition features may be incorporated at transition locations along finger clutch 206, such as a fillet between cylindrical hub 806 and disc portion 808, or a chamfered or curved edge along an outer edge of disc portion 808. In an embodiment, distal portion has a disc diameter 810 about central axis 404 that is larger than the maximum diameter of device housing 202, e.g., the diameter of ridge 310. Capacitive sensing region 802 may extend along an outer edge of disc portion 808 and not over a proximal wall of disc portion 808 or cylindrical hub 806. Accordingly, user 107 may rest an extended finger against cylindrical hub 806 or the proximal wall of disc portion 808 without triggering the finger clutch 206. The shape of finger clutch 206 shown in FIG. 8C can allow user 107 to reach toward the edge of disc portion 808 at a distance greater than the maximum diameter of device housing 202 to trigger finger clutch 206. Such finger extension may require greater volition by user 107, and thus, can reduce a likelihood of false triggering of finger clutch 206.

Figure 8D:
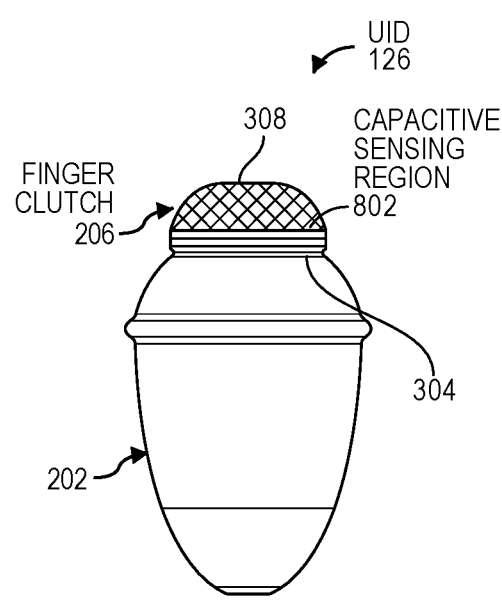

Referring to FIG. 8D, a side view of a UID 126 having an alternative finger clutch shape is shown. In an embodiment, second surface of revolution 412 of finger clutch 206 may have a convex outward shape between housing end 304 and distal tip 308. The convex outward shape may have a radius about central axis 404 that reduces between housing end 304 and distal tip 308. Capacitive sensing region 802 of finger clutch 206 may extend over a distal portion of finger clutch 206.

Figure 8E:
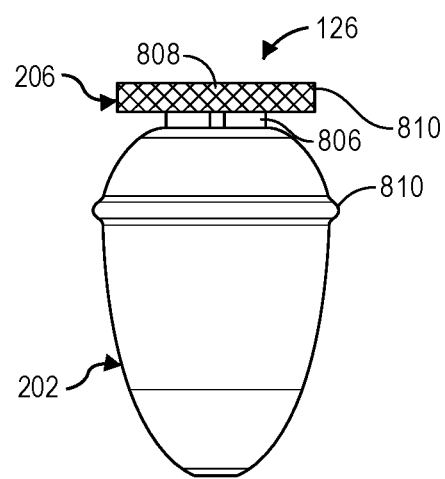

Referring to FIG. 8E, a side view of a UID 126 having an alternative finger clutch shape is shown. In an embodiment, finger clutch 206 includes a cylindrical hub 806 near housing end 304 and a disc portion 808 at distal tip 308. Cylindrical hub 806 may have a constant radius about central axis 404 over a length between housing end 304 and disc portion 808. Similarly, disc portion 808 may have a constant radius about central axis 404 over a length between cylindrical hub 806 and distal tip 308. In contrast to FIG. 8C, disc portion 808 of FIG. 8E may not include transition features. For example, an outer edge of disc portion 808 may have a straight cylindrical wall, rather than a curved wall. In an embodiment, distal portion has a disc diameter 810 about central axis 404 that is smaller than the maximum diameter of device housing 202. Capacitive sensing region 802 may extend along an outer edge of disc portion 808 and not over a proximal wall of disc portion 808 or over cylindrical hub 806. Accordingly, user 107 may rest an extended finger against cylindrical hub 806 or the proximal wall of disc portion 808 without triggering the finger clutch 206. The shape of finger clutch 206 shown in FIG. 8E can allow user 107 to reach toward the edge of disc portion 808 to trigger finger clutch 206. Such finger extension may require greater volition by user 107, and thus, can reduce the likelihood of false triggering of finger clutch 206.

Finger clutch 206 includes a capacitive sensor that advantageously does not require application of force to actuate. As described above, actuating a switch that requires an actuation force or pressure can cause unintentional movements of surgical robotic arm 112. By contrast, the capacitive sensor of finger clutch 206 can be actuated when user 107 lightly places a finger on clutch cover 410. Such actuation can be advantageous, however, false triggering of the capacitive sensor should be avoided. As described above, finger clutch 206 may be shaped and configured to reduce the likelihood of false triggering of the clutch mechanism. For example, conductive pad(s) 502 can be located to form capacitive sensing region 802 at locations that are less likely to be accidentally touched by user 107 during use of UID 126. The likelihood of false triggering may also be reduced by requiring user gestures that are indicative of user volition.

UID processor 606 may be configured to determine, in response to a change in the capacitance of conductive pad 502, that a predetermined touch gesture has been performed by user 107. More particularly, the predetermined touch gesture of clutch cover 410 by user 107 may be determined by UID processor 606. In an embodiment, UID processor 606 is configured to determine the predetermined touch has occurred when the change of capacitance is for a predetermined period of time. For example, UID processor 606 may detect a long tap on finger clutch 206 by user 107. The long tap may be a gesture by user 107 that includes resting an extended finger on capacitive sensing region 802 for the predetermined period of time, e.g., at least 0.5 seconds. When the change of capacitance detected by UID processor 606 is greater than a predetermined threshold for the predetermined period of time, UID processor 606 can determine that user 107 has touched clutch cover 410. Accordingly, UID processor 606 can generate a clutch signal that is transmitted to computer system 110. The clutch signal can be a clutch activation signal to pause motion of surgical robotic arm 112, as described above.

It will be appreciated that finger clutch 206 may include one or more sensor types to detect a touch by user 107. More particularly, although finger clutch 206 has been primarily described as including a capacitive sensor, finger clutch 206 may incorporate a different type of sensor to determine that user 107 has touched outer touch surface 508. In an embodiment, finger clutch 206 includes a proximity sensor to detect a presence of the finger of user 107. Accordingly, finger clutch 206 can include an emitter to emit an electromagnetic field or a beam of electromagnetic radiation, and a receiver to detect a return signal from the emission. By way of example, finger clutch 206 may include an optical emitter and an optical receiver to detect the touch by user 107. Accordingly, the embodiments described above encompass finger clutch 206 having sensors of different types that detect touch based on a presence or proximity of an object without requiring the detection of a threshold force applied by the object on finger clutch 206.

Figure 9:
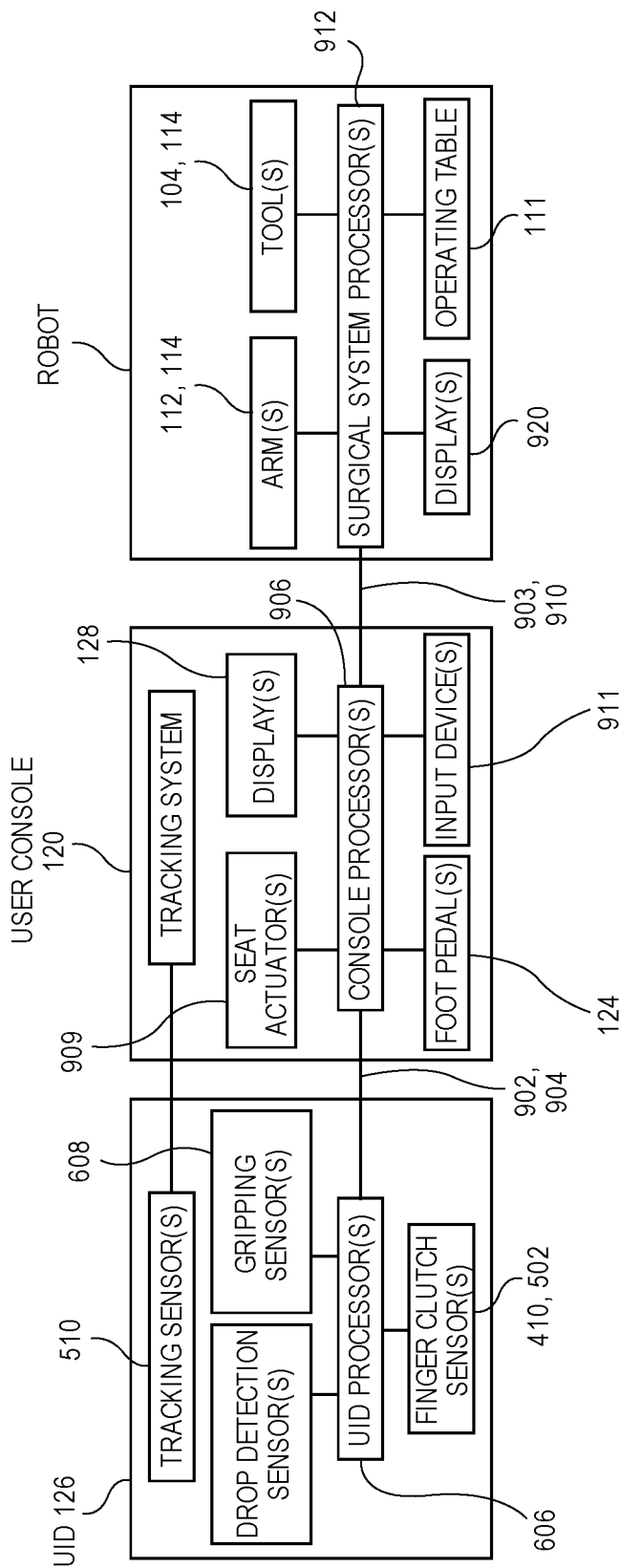
FIG. 9 is a block diagram of a computer portion of a surgical robotic system, in accordance with an embodiment.

Referring to FIG. 9, a block diagram of a computer portion of a surgical robotic system is shown in accordance with an embodiment. Surgical robotic system 100 can include UID(s) 126, user console 120 having computer system 110, and robotic components 104, 112. Computer system 110 and UID 126 have circuitry suited to specific functionality, and thus, the diagrammed circuitry is provided by way of example and not limitation.

One or more processors of user console 120 can control portions of surgical robotic system 100, e.g., surgical robotic arms 112 and/or surgical tools 104. UID 126 may be communicatively coupled to computer system 110 and/or surgical robotic system 100 to provide input commands that are processed by one or more processors of system 100 to control movement of surgical robotic arm 112 and/or surgical tool 104 mounted on the arm. For example, UID 126 may communicate electrical command signals 902 to computer system 110, e.g., spatial state signals generated by UID processor 606 in response to signals from tracking sensor 510, or clutch signals generated by UID processor 606 in response to detected changes in capacitance of conductive pad 502 of finger clutch 206. The electrical signals may be input commands to cause motion of surgical robotic system 100, or to pause motion of surgical robotic system 100.

The input electrical signals may be transmitted by UID processor 606 to a console processor 906 of computer system 110 via a wired or wireless connection. For example, UID 126 may transmit the command signals 902 to console processor 906 via electrical wire. Alternatively, UID 126 may transmit command signals 902 to console processor 906 via a wireless communication link. The wireless communication link may be established by respective RF circuitry of computer system 110 and UID 126. The wireless communication can be via radiofrequency signals, e.g., Wi-Fi or short range signals and/or suitable wireless communication protocols such as Bluetooth.

Console processor 906 of computer system 110 may execute instructions to carry out the different functions and capabilities described above. Instructions executed by console processor(s) 906 of user console 120 may be retrieved from a local memory (not shown), which may include a non-transitory machine-readable medium. The instructions may be in the form of an operating system program having device drivers to control components of surgical robotic system 100, e.g., actuators 114 operatively coupled to surgical robotic arm(s) 112 or surgical tool(s) 104.

In an embodiment, console processor 906 controls components of user console 120. For example, one or more seat actuators 909 can receive commands from console processor 906 to control movement of seat 122. Seat actuator(s) 909 can move seat 122 in one or more degrees of freedom, such as forward/backward, backrest tilt, headrest position, etc. Console processor 906 can also transmit video data for presentation on display 128. Accordingly, console processor 906 can control operation of user console 120. Input commands to seat actuator(s) 909 or console processor 906 can be entered by the user via foot pedal(s) 124 or another input device 911 such as a keyboard or a joystick.

Console processor 906 can output control signals 903 to other components of surgical robotic system 100 via a link 910. Control signals 903 may be transmitted to control movement of surgical robotic system 100. In an embodiment, computer system 110 is communicatively coupled to downstream components of surgical robotic system 100, e.g., control tower 130, via wired or wireless links. The links can transmit control signals 903 to one or more surgical system processor(s) 912. For example, at least one processor 912 can be located in control tower 130, and may be communicatively coupled to system components, such as surgical robotic platform 111 or one or more displays 920. Actuators 114 of surgical robotic system 100 may receive control signals from surgical system processor 912 to cause movement of arm 112 and/or tool 104 corresponding to movement of UID 126. The control signals can also pause motion of the robotic components by clutching and/or disconnecting an interlock of surgical robotic system 100 when user 107 touches finger clutch 206 or drops UID 126.

A method of using UID 126 having finger clutch 206 to cause motion of surgical robotic system 100 is provided below. It will be appreciated that this method summarizes operations previously described, and does not include every operation described. Accordingly, the method described below is provided by way of illustration and not limitation.

At an operation, UID processor 606 receives spatial state signals from tracking sensor 510 and/or the grip signal from gripping sensor 608. The signals can be transmitted by UID processor 606 to one or more processors of user console 120 and/or control tower 130. The one or more processors can process the input signals to generate output control signals. The output control signals can cause movement of actuators 114, which can move arm 112 and/or tool 104. The movement may be based on spatial state signals 904 and/or the grip signal. For example, actuators 114 can move surgical robotic arm 112 in response to the generation of spatial state signals 904. Similarly, actuators 114 can move surgical tool 104 in response to the grip signal. For example, a grasper of surgical tool 104 may close when the grip signal represents the operator 107 squeezing device housing 202. Surgical tool 104 may be coupled to arm 112, and thus, movement of actuators 114 can move both surgical robotic arm 112 and surgical tool 104.

At an operation, UID processor 606 can detect a capacitance of conductive pad 502. At an operation, UID processor 606 can determine, in response to a change in the capacitance of the conductive pad, a touch by a user. UID processor 606 may generate a clutch signal 902, e.g., a clutch activation signal, in response to determining the touch.

One or more processors of surgical robotic system 100 can receive and process clutch signal 902 from UID 126, e.g., via computer system 110. Surgical robotic system 100 can pause movement of one or more of actuators 114 in response to the clutch signal 902. The movement can be stopped regardless of spatial state signals 904 and/or the grip signal. For example, user 107 may move UID 126 to a new location without causing a corresponding movement of surgical robotic arm 112 or surgical tool 104. Similarly, the squeeze exerted by the user may change when finger clutch 206 is touched, but there may be no corresponding change in the opened or closed position of the grasper of surgical tool 104. Accordingly, finger clutch 206, which may be a touch sensor, can pause teleoperation of surgical robotic arm 112 and surgical tool 104 in all seven degrees of freedom detected by UID 126.

UID processor 606 can determine other user gestures based on detected capacitances. For example, UID processor 606 may detect a sequence of changes in respective capacitances of a first conductive pad 502 and a second conductive pad 702. For example, a capacitance of the first conductive pad 502 may change at a first time, and a capacitance of the second conductive pad 702 may change at a second time after the first time. In response to detecting the sequence of changes of the respective capacitances, UID processor 606 may determine that user 107 has made a swipe gesture. An input signal, e.g., clutch signal 902, may be generated by UID processor 606 in response to determining the swipe gesture by user 107, and the input signal can be used by the processor(s) of surgical robotic system 100 to control motion or another operation of surgical robotic system 100.

Figure 10:
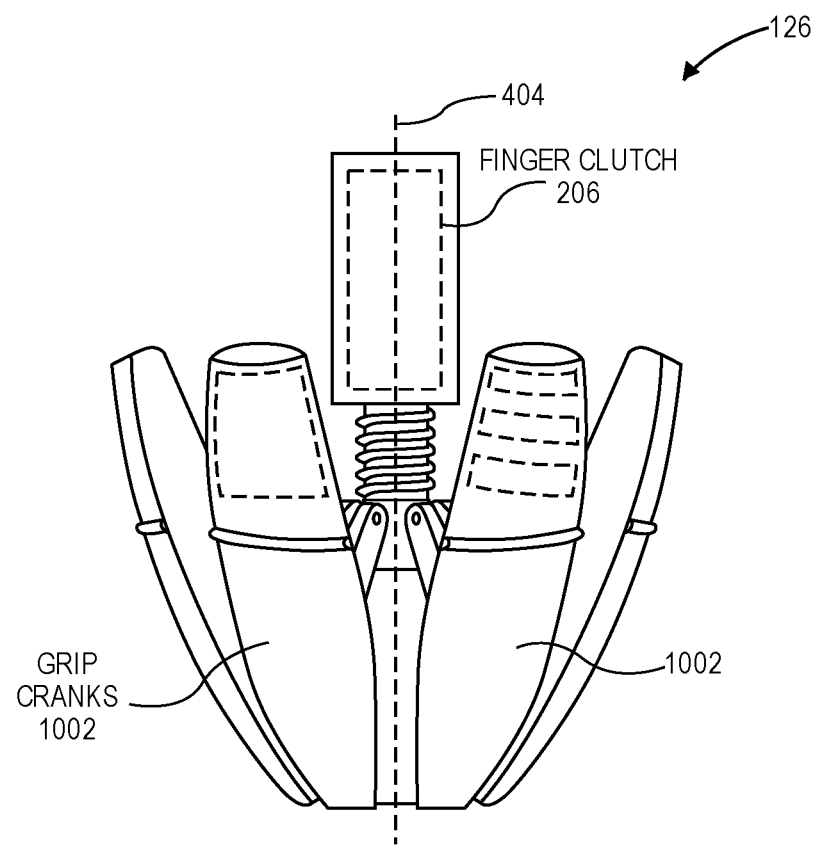
FIG. 10 is a side view of a user interface device having grip linkages, in accordance with an embodiment.

Referring to FIG. 10, a side view of a user interface device having grip linkages is shown in accordance with an embodiment. Finger clutch 206 can be incorporated into UID 126 having grip linkages that may be finger-held and manipulated to provide highly dexterous, precise movements of a surgical tool of a surgical robotic system. For example, alternative embodiments of UID 126 are described in U.S. patent application Ser. No. 16/010,054 titled "USER INTERFACE DEVICE HAVING GRIP LINKAGES," which was filed on Jun. 15, 2018. Such embodiments of UID 126 can include several grip cranks 1002 that are used to command operation of surgical robotic system 100, as described in that application. In an embodiment, finger clutch 206 can be incorporated into the alternative embodiments of UID 126 to provide the functionality described above, e.g., to pause the system operation. Accordingly, it will be appreciated that finger clutch 206 can be incorporated into any design of UID 126, and the various embodiments of UID 126 described above are to be regarded in an illustrative and not a restrictive sense.

In the foregoing specification, the invention has been described with reference to specific exemplary embodiments thereof. It will be evident that various modifications may be made thereto without departing from the broader spirit and scope of the invention as set forth in the following claims.

The specification and drawings are, accordingly, to be regarded in an illustrative sense rather than a restrictive sense.

What is claimed is:

1. A user interface device for manipulating a surgical tool in a surgical robotic system, comprising:
   a device housing having a gripping surface, wherein the gripping surface is radially symmetric about an axis of symmetry;
   a tracking sensor in the device housing, wherein the tracking sensor is configured to generate a plurality of spatial state signals tracking movement of the device housing in six degrees of freedom to control motion of the surgical tool; and
   a finger clutch having a touch-sensitive surface facing radially outward from the axis of symmetry, wherein the finger clutch is configured to, when touched, generate a clutch signal to cause one or more processors of the surgical robotic system to pause motion of the surgical tool regardless of the plurality of spatial state signals.

2. The user interface device of claim 1, wherein the gripping surface is revolved about the axis of symmetry.

3. The user interface device of claim 2, wherein the device housing has an ovoid shape.

4. The user interface device of claim 2, wherein the device housing includes a plurality of grip cranks, and wherein the gripping surface is on an outer surface of the grip cranks.

5. The user interface device of claim 1 further comprising a gripping sensor configured to, when squeezed, generate a grip signal to cause a grip motion of the surgical tool, wherein the finger clutch, when activated, generates the clutch signal regardless of the grip signal.

6. The user interface device of claim 1, wherein the touch-sensitive surface of the finger clutch is a surface of revolution about the axis of symmetry.

7. The user interface device of claim 6, wherein the surface of revolution is frustoconical.

8. The user interface device of claim 7, wherein the surface of revolution comprises a longitudinal gap.

9. The user interface device of claim 1, wherein the finger clutch includes a conductive pad extending around the axis of symmetry, and wherein the finger clutch includes a clutch cover over the conductive pad.

10. The user interface device of claim 9 further comprising a user interface device processor configured to:
    measure a capacitance of the conductive pad, and
    generate the clutch signal in response to detecting a change in the capacitance.

11. A surgical robotic system, comprising:
    a surgical tool;
    a user interface device including
       a device housing having a gripping surface, wherein the gripping surface is radially symmetric about an axis of symmetry,
       a tracking sensor in the device housing, wherein the tracking sensor is configured to generate a plurality of spatial state signals tracking movement of the device housing in six degrees of freedom to control motion of the surgical tool, and
       a finger clutch having a touch-sensitive surface facing radially outward from the axis of symmetry, wherein the finger clutch is configured to, when touched, generate a clutch signal; and
    one or more processors communicatively coupled to the user interface device and the surgical tool, wherein the processors are configured to control spatial motion of the surgical tool based on at least one of the plurality of spatial state signals or the clutch signal, and wherein the clutch signal causes the one or more processors to pause the spatial motion of the surgical tool regardless of the plurality of spatial state signals.

12. The surgical robotic system of claim 11, wherein the gripping surface is revolved about the axis of symmetry.

13. The surgical robotic system of claim 12, wherein the device housing has an ovoid shape.

14. The surgical robotic system of claim 12, wherein the device housing includes a plurality of grip cranks, and wherein the gripping surface is on an outer surface of the grip cranks.

15. The surgical robotic system of claim 11 further comprising a gripping sensor configured to, when squeezed, generate a grip signal to cause a grip motion of the surgical tool, wherein the finger clutch, when activated, generates the clutch signal regardless of the grip signal.

16. The surgical robotic system of claim 11, wherein the touch-sensitive surface of the finger clutch is a surface of revolution about the axis of symmetry.

17. The surgical robotic system of claim 16, wherein the surface of revolution is frustoconical.

18. The surgical robotic system of claim 17, wherein the surface of revolution comprises a longitudinal gap.

19. The surgical robotic system of claim 11, wherein the finger clutch includes a conductive pad extending around the axis of symmetry, and wherein the finger clutch includes a clutch cover over the conductive pad.

20. The surgical robotic system of claim 19, wherein the user interface device includes a user interface device processor configured to:
    measure a capacitance of the conductive pad, and
    generate the clutch signal in response to detecting a change in the capacitance.

* * * * *